United States Patent
Seo et al.

(10) Patent No.: US 12,397,082 B2
(45) Date of Patent: Aug. 26, 2025

(54) ANTIMICROBIAL DRESSING

(71) Applicant: AMOGREENTECH CO., LTD., Gimpo-si (KR)

(72) Inventors: In Yong Seo, Seoul (KR); Seung Hoon Lee, Paju-si (KR); Song Hee Koo, Seoul (KR); Ji Hyun Lee, Incheon (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 394 days.

(21) Appl. No.: 18/169,397

(22) Filed: Feb. 15, 2023

(65) Prior Publication Data
US 2023/0190989 A1 Jun. 22, 2023

Related U.S. Application Data

(63) Continuation-in-part of application No. 15/559,667, filed as application No. PCT/KR2016/005293 on May 19, 2016, now abandoned.

(30) Foreign Application Priority Data

Jun. 1, 2015 (KR) ........................ 10-2015-0077316

(51) Int. Cl.
*A61L 15/44* (2006.01)
*A61L 15/18* (2006.01)
(Continued)

(52) U.S. Cl.
CPC ............... *A61L 15/44* (2013.01); *A61L 15/18* (2013.01); *A61L 15/225* (2013.01);
(Continued)

(58) Field of Classification Search
CPC ........ A61L 15/44; A61L 15/18; A61L 15/225; A61L 15/425; A61L 2300/104; A61L 2300/404; A61L 2400/12; A61L 15/46
See application file for complete search history.

(56) References Cited

U.S. PATENT DOCUMENTS 4,308,303 A * 12/1981 Mastroianni ........... A61B 46/40
442/370
4,750,482 A * 6/1988 Sieverding ................. C09J 7/10
602/56

(Continued)

FOREIGN PATENT DOCUMENTS

| CN | 117838909 A | * 4/2024 |
|---|---|---|
| KR | 20100021108 | 2/2010 |
| KR | 20140117293 | 10/2014 |

OTHER PUBLICATIONS

International Search Report—PCT/KR2016/005293 dated Aug. 8, 2016.

*Primary Examiner* — Tarla R Patel
(74) *Attorney, Agent, or Firm* — CANTOR COLBURN LLP

(57) ABSTRACT

Provided is an antimicrobial dressing, which includes: a first cover member having a plurality of pores formed therein and contacting a wound; an antimicrobial membrane that is made by accumulating nanofibers containing a water-soluble polymer that is dissolved in an exudate secreted from the wound, a water-insoluble polymer, and an antimicrobial substance released due to dissolution of the water-soluble polymer, the antimicrobial membrane being laminated on the first cover member and having a plurality of pores formed therein; and a second cover member laminated on the antimicrobial membrane and having a plurality of pores formed therein and exposed to an external air.

16 Claims, 3 Drawing Sheets

(51) Int. Cl.
*A61L 15/22* (2006.01)
*A61L 15/42* (2006.01)

(52) U.S. Cl.
CPC ....... *A61L 15/425* (2013.01); *A61L 2300/104* (2013.01); *A61L 2300/404* (2013.01); *A61L 2400/12* (2013.01)

(56) References Cited

U.S. PATENT DOCUMENTS

| | | | |
|---|---|---|---|
| 4,860,737 A | 8/1989 | Lang et al. | |
| 4,997,425 A | 3/1991 | Shioya et al. | |
| 6,168,800 B1 | 1/2001 | Dobos et al. | |
| 7,270,721 B2 * | 9/2007 | Hilfenhaus | A61F 13/8405 156/60 |
| 2003/0040691 A1 * | 2/2003 | Griesbach, III | B32B 5/26 602/45 |
| 2003/0104039 A1 | 6/2003 | Berthold et al. | |
| 2004/0014413 A1 * | 1/2004 | Kawahashi | B24B 37/26 451/527 |
| 2004/0063391 A1 * | 4/2004 | Hosaka | C08L 23/0853 451/526 |
| 2004/0118051 A1 * | 6/2004 | Shiho | B24B 37/24 451/533 |
| 2006/0020235 A1 * | 1/2006 | Siniaguine | A61F 13/0289 602/41 |
| 2007/0286895 A1 | 12/2007 | Bowler et al. | |
| 2008/0167594 A1 | 7/2008 | Siniaguine | |
| 2010/0178489 A1 | 7/2010 | Nishiyama et al. | |
| 2010/0215939 A1 * | 8/2010 | Westbroek | D04H 3/16 428/292.1 |
| 2010/0298793 A1 * | 11/2010 | Blott | A61F 13/0213 604/319 |
| 2012/0102725 A1 * | 5/2012 | Fuller | H01M 50/414 29/623.1 |
| 2013/0018336 A1 * | 1/2013 | Pernot | A61F 13/445 424/445 |
| 2015/0072008 A1 * | 3/2015 | Tornero Garcia | A61K 9/70 604/289 |

* cited by examiner

ANTIMICROBIAL DRESSING

TECHNICAL FIELD

The present invention relates to dressing, and more particularly, to an antimicrobial dressing for treating a wound, in which an antimicrobial substance is slowly released by using a water-soluble polymer to be dissolved in an exudate to reduce the amount of the antimicrobial substance contacting the wound to thereby maximize antimicrobial properties on the wound surface while relieving pain.

BACKGROUND ART

Generally, if a wound is generated, after the wound is disinfected, the dressing for wound treatment is fixed with a medical tape so that the surface of the wound is sufficiently covered according to the amount of exudates generated from the wound.

The dressing for wound treatment protects the wound, absorbs the exudate, promotes hemostasis, and supports the wound. It covers the wound surface, which is a skin defect area due to burns, cuts, bedsores and external wounds, to thereby improve a treatment speed.

Recently, research on dressing to provide an optimal treatment environment has been continuously carried out, and development of a dressing capable of imparting various functions is also needed.

Korean Patent Laid-open Publication No. 2010-0021108 discloses an antimicrobial dressing laminate as a laminate comprising: a silver nanoparticle-containing nanofiber member; an exudate absorbing member laminated on top of the nanofiber member; and a cover member formed of a semitransparent film and laminated on the exudate absorbing member, wherein the spinning solution in which the silver nanoparticle-containing nanofiber member comprises nanofibers that are manufactured in a web form having a fiber diameter of less than 1 μm by electrospinning a spinning solution containing a fiber-forming polymer and a silver (Ag) metallic salt. Accordingly, the dressing having an antimicrobial activity may be realized but the silver nanoparticles are bound to the nanofibers of the nanofiber member. As a result, there is a disadvantage the silver nanoparticle-containing nanofiber member exhibits an effective antimicrobial effect only at a laminated position of the laminate and exposes a slight antimicrobial characteristic at the wound surface.

DISCLOSURE

Technical Problem

The present invention has been made in view of the above-mentioned defects, and it is an object of the present invention to provide an antimicrobial dressing which can reduce the amount of an antimicrobial substance to contact the wound and reduce the pain while maximizing the antimicrobial characteristic on a wound surface in which a water-soluble polymer which can be dissolved by an exudate secreted from the wound and the antimicrobial substance which is slowly released by dissolution of the water-soluble polymer are included in nanofibers of a membrane.

Another object of the present invention is to provide an antimicrobial dressing capable of adsorbing heavy metal ions, bacteria, and viruses penetrating from the outside of a dressing.

Technical Solution

In order to accomplish the above object, according to an aspect of the present invention, there is provided an antimicrobial dressing comprising: a first cover member having a plurality of pores formed therein and contacting a wound; an antimicrobial membrane that is made by accumulating nanofibers containing a water-soluble polymer that is dissolved in an exudate secreted from the wound, a water-insoluble polymer, and an antimicrobial substance released due to dissolution of the water-soluble polymer, the antimicrobial membrane being laminated on the first cover member and having a plurality of pores formed therein; and a second cover member laminated on the antimicrobial membrane and having a plurality of pores formed therein and exposed to an external air.

In the antimicrobial dressing according to an embodiment of the present invention, the antimicrobial substance may be one of a silver nanomaterial, a silver particle, and a natural antimicrobial substance.

In the antimicrobial dressing according to an embodiment of the present invention, the water-soluble polymer may be at least one or a mixture of two or more selected from the group consisting of PVA (polyvinyl alcohol), PVP (polyvinyl pyrrolidone), PEO (polyethylene oxide), CMC (carboxyl methyl cellulose), starch, PAA (polyacrylic acid) and a hyaluronic acid.

In the antimicrobial dressing according to an embodiment of the present invention, the first and second cover members may be one of a nonwoven fabric, a fabric, and a mesh.

In the antimicrobial dressing according to an embodiment of the present invention, the antimicrobial membrane comprises: a support member; a first membrane member formed by accumulating the nanofibers containing the water-soluble polymer, the water-insoluble polymer, and the antimicrobial substance on one surface of the support member; and a second membrane member formed by accumulating the nanofibers made of the water-insoluble polymer on the other surface of the support member.

In the antimicrobial dressing according to an embodiment of the present invention, the support member may be one of a nonwoven fabric, a fabric, and a mesh.

In the antimicrobial dressing according to an embodiment of the present invention, the antimicrobial membrane comprises: a first membrane member made by accumulating the nanofibers containing the water-soluble polymer, the synthetic polymer, and the antimicrobial substance; and a second membrane member formed by accumulating the nanofibers made of the water-insoluble polymer on the first membrane member.

In the antimicrobial dressing according to an embodiment of the present invention, the first membrane member is a multilayer structure in which each layer is formed by accumulating the nanofibers containing the water-soluble polymer, the water-insoluble polymer, and the antimicrobial substance, and as the layer becomes closer to the wound, the water-soluble polymer content may be increased.

In the antimicrobial dressing according to an embodiment of the present invention, a plurality of pores may be formed in the first membrane member and a nanofiber web formed by accumulating the nanofibers containing dopamine having a functional group capable of adsorbing ionic foreign substances, bacteria, and viruses, or a nanofiber web formed by accumulating ion-exchange nanofibers may be further stacked.

In the antimicrobial dressing according to an embodiment of the present invention, the first and second membrane members may have different diameters and pore sizes of the nanofibers.

In the antimicrobial dressing according to an embodiment of the present invention, the diameters of the nanofibers of the first membrane member may range from 200 nm to 800 nm, and the diameters of the nanofibers of the second membrane member may be less than 200 nm.

In the antimicrobial dressing according to an embodiment of the present invention, the pore size of the first membrane member may range from 0.2 μm to 1 μm, and the pore size of the second membrane member may be less than 0.2 μm.

Advantageous Effects

According to the present invention, an antimicrobial membrane produced by accumulating nanofibers containing a water-soluble polymer and an antimicrobial substance is realized as a dressing for wound treatment, so that the water-soluble polymer is dissolved in the exudates secreted from the wound, and the antimicrobial substance is released slowly, to thereby reduce the amount of the antimicrobial substance contacting the wound, thus reducing the pain and improving an antimicrobial characteristic on the wound surface.

According to the present invention, it is possible to control the rate at which the antimicrobial substance is released by controlling the content of the water-soluble polymer of a laminated structure, thereby preventing a large amount of the antimicrobial substance from contacting the wound.

According to the present invention, a nanofiber web formed by accumulation of nanofibers containing dopamine having a functional group, or a nanofiber web formed by accumulation of ion-exchanged nanofibers is included in a dressing, thereby providing an advantage of adsorbing ionic foreign matters of heavy metals, bacteria, viruses and the like, impregnated from the outside of the dressing.

According to the present invention, a membrane member having excellent air permeability is included in a dressing to provide an optimal wetting environment, thereby preventing substances that are involved in treatment, such as polynuclear leukocytes, macrophages, proteolytic enzymes, or cell growth factors, from being discharged out or being dried, to thus efficiently perform the wound treatment.

BEST MODE

Hereinafter, embodiments of the present invention will be described in detail with reference to the accompanying drawings.

Figure 1:
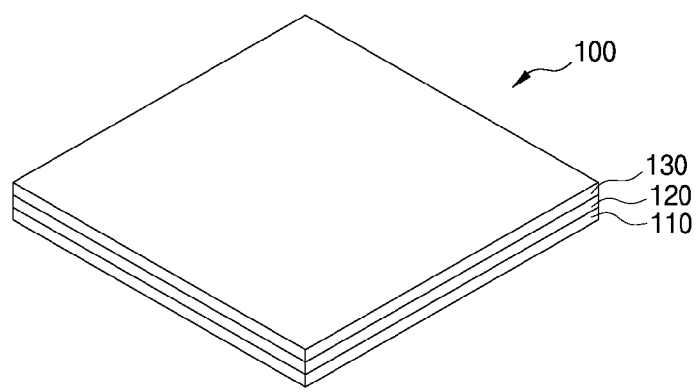
FIG. 1 is a perspective view of an antimicrobial dressing according to an embodiment of the present invention.

Referring to FIG. 1, an antimicrobial dressing 100 according to an embodiment of the present invention includes: a first cover member 110 having a plurality of pores and contacting a wound; an antimicrobial membrane 120 that is made by accumulating nanofibers containing a water-soluble polymer that is dissolved in an exudate secreted from the wound, a water-insoluble polymer, and an antimicrobial substance released due to dissolution of the water-soluble polymer, the antimicrobial membrane being laminated on the first cover member 110 and having a plurality of pores formed therein; and a second cover member 130 laminated on the antimicrobial membrane 120 and having a plurality of pores formed therein and exposed to an external air.

Accordingly, the water-soluble polymer contained in the nanofibers of the antimicrobial membrane 120 is gradually dissolved in the exudate, and thus the antimicrobial substance contained in the nanofibers is gradually released so that a small amount of the antimicrobial substance comes into contact with the wound, to thereby maximize an antimicrobial characteristic inside the antimicrobial membrane 120 and on the wound surface, while reducing the pain.

That is, when silver is coated on the dressing to allow excessive silver to release from a silver coating surface of the antimicrobial dressing, excessive silver may be brought into contact with the wound, so that the patient may feel a great pain, while the antimicrobial dressing according to the embodiment of the present invention has a small amount of the antimicrobial substance slowly released and comes into contact with the wound, to thereby relieve the pain that the patient may feel.

The antimicrobial membrane 120 is formed of a nanofiber web having a plurality of pores made by accumulating nanofibers obtained by electrospinning a spinning solution containing a water-soluble polymer, a water-insoluble polymer, and an organic solvent.

The water-soluble polymer may include one or a mixture of two or more selected from polyvinyl alcohol (PVA), polyvinyl pyrrolidone (PVP), polyethylene oxide (PEO), carboxyl methyl cellulose (CMC), starch, polyacrylic acid (PAA), and hyaluronic acid.

The antimicrobial substance is preferably one of natural antimicrobial substances such as silver nanomaterials, silver particles and chitosan. Here, silver nanomaterials are silver (Ag) salts such as silver nitrate ($AgNO_3$), silver sulfate ($Ag_2SO_4$), and silver chloride (AgCl).

Then, silver particles of the diameters smaller than the diameters of the nanofibers can be selected and used so that the silver particles can be dispersed in the nanofibers.

The water-insoluble polymer is capable of electrospinning and is intended to maintain the structure of the antimicrobial membrane 120 even if the water-soluble polymer is dissolved in the exudate and the antimicrobial substance is released. In addition, the water-insoluble polymer can be dissolved in an organic solvent for electrospinning and is not particularly limited as long as it is a resin capable of forming nanofibers by electrospinning. For example, the water-insoluble polymer may include: polyvinylidene fluoride (PVdF), poly (vinylidene fluoride-co-hexafluoropropylene), perfluoropolymers, polyvinyl chloride or polyvinylidene chloride, and co-polymers thereof.

In addition, examples of the usable water-insoluble polymer may include: aromatic polyester such as polyamide, polyimide, polyamide-imide, poly (meta-phenylene isophthalamide), polysulfone, polyether ketone, polyethylene terephthalate, polytrimethylene terephthalate, and polyethylene naphthalate; polyphosphazenes such as polytetrafluoroethylene, polydiphenoxy phosphazene, and poly {bis [2-(2-methoxyethoxy) phosphazene]}; polyurethane co-polymers including polyurethane and polyether urethane; cellulose acetate, cellulose acetate butylrate, cellulose acetate propionate, and the like.

The solvent may employ at least one selected from the group consisting of DMAc (N, N-dimethyl acetoamide), DMF (N, N-dimethylformamide), NMP (N-methyl-2-pyrrolidinone), DMSO (dimethyl sulfoxide), THF (tetra-hydrofuran), EC (ethylene carbonate), DEC (diethyl carbonate), DMC (dimethyl carbonate), EMC (ethyl methyl carbonate), PC (propylene carbonate), water, acetic acid, formic acid, chloroform, dichloromethane, acetone, and isopropylalchol.

The first and second cover members 110 and 130 may employ one of a nonwoven fabric, a fabric, and a mesh.

Figure 2:
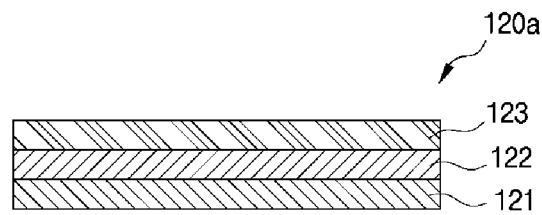
FIG. 2 is a cross-sectional view of an antimicrobial membrane applied to an antimicrobial dressing according to a first embodiment of the present invention.
Figure 3:
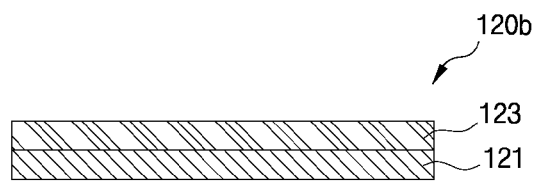
FIG. 3 is a cross-sectional view of an antimicrobial membrane applied to an antimicrobial dressing according to a second embodiment of the present invention.

FIGS. 2 and 3 are cross-sectional views of antimicrobial membranes applied to the antimicrobial dressing according to of the first and second embodiments of the present invention.

Referring to FIG. 2, an antimicrobial membrane 120a applied to the antimicrobial dressing according to the first embodiment of the present invention includes a support member 122, a first membrane member 121 laminated on one surface of the support member 122, in which the first membrane member 121 is made by accumulating nanofibers containing a water-soluble polymer, a water-insoluble polymer, and an antimicrobial substance, and a second membrane member 123 laminated on the other surface of the support member 122 in which the second membrane member 123 is made by accumulating nanofibers made of the water-insoluble polymer.

The first and second membrane members 121 and 123 are nanofiber webs formed by accumulating nanofibers obtained by electrospinning and formed with a plurality of pores.

The first membrane member 121 is realized as a nanofiber web formed by dissolving a water-soluble polymer, a water-insoluble polymer, and an antimicrobial substance, in an organic solvent to prepare a spinning solution, and electrospinning the spinning solution to accumulate nanofibers containing the antimicrobial substance.

The second membrane member 123 may be realized as a nanofiber web formed by dissolving a water-insoluble polymer in an organic solvent to prepare a spinning solution and electro spinning the spinning solution to accumulate nanofibers containing the water-insoluble polymer.

That is, the first membrane member 121 may contain the water-soluble polymer dissolved in the exudate and the antimicrobial substance to be released to thereby have an excellent antimicrobial characteristic. Here, the first membrane member 121 is close to the wound.

The second membrane member 123 is designed so that it does not contain an antimicrobial substance and a water-soluble polymer, and it does not affect the exudates. The second membrane member 123 is formed of ultra-fine pores having excellent air permeability, through which the exudates do not pass but only the outside air can pass.

Meanwhile, substances involved in treatment such as polymorphonuclear leukocytes, macrophages, proteolytic enzymes, and cell growth factors contained in the exudates are discharged or dried out in a dry environment and thus do not perform their functions.

Therefore, the second membrane member 123 having excellent air permeability provides an optimal wetting environment to the wound surface, so that wound treatment can be efficiently performed.

The support member 122 may employ one of a nonwoven fabric, a fabric, and a mesh.

Referring to FIG. 3, the antimicrobial membrane 120b applied to the antimicrobial dressing according to the second embodiment of the present invention includes a first membrane member 121 made by accumulating nanofibers containing a water-soluble polymer, a water-insoluble polymer, and an antimicrobial substance, and a second membrane member 123 formed by accumulating nanofibers made of a water-insoluble polymer, in which the second membrane member 123 is laminated on the first membrane member 121.

The antimicrobial membrane 120b according to the second embodiment is made by forming the first membrane member 121 into a first nanofiber web by electrospinning, and then forming the second membrane member 123 on the first membrane member 121 by electrospinning.

The antimicrobial membrane 120a applied to the antimicrobial dressing according to the first embodiment of the present invention described above has a three-layer structure in which the support member 122 is interposed between the first and second membrane members 121 and 123. Thus, the strength of the antimicrobial membrane 120a is increased by the support member 122 and the handling property is improved.

Accordingly, the antimicrobial membrane 120b according to the second embodiment can be realized as a thin antimicrobial membrane 120b with a two-layer structure in which the first and second membrane members 121 and 123 are laminated.

FIGS. 4 to 7 are cross-sectional views for explaining modifications of the membrane member applied to the antimicrobial membrane according to the first and second embodiments of the present invention.

Figure 4:
FIG. 4 is a cross-sectional view for explaining a first modification of a membrane member applied to the antimicrobial membrane according to the first and second embodiments of the present invention.

Referring to FIG. 4, the first membrane member 121 of FIGS. 2 and 3 that may be applied to the antimicrobial membranes of the first and second embodiments controls the rate at which the antimicrobial substance is released by controlling the content of the water-soluble polymer so that a large amount of the antimicrobial substance can be prevented from contacting the wound.

That is, the first membrane member 121 of FIGS. 2 and 3 includes at least two or more multi-layered structures in which each layer is formed by accumulating nanofibers containing a water-soluble polymer, a water-insoluble polymer, and an antimicrobial substance, and as the layer becomes closer to the wound, the water-soluble polymer content may be increased.

For example, when the first membrane member 121 of FIGS. 2 and 3 is formed of a two-layer laminated structure of first and second layers 121*a* and 121*b*, as shown in FIG. 4, the first layer 121*a* closer to the wound, has the water-soluble polymer content higher than the second layer 121*b*.

Figure 5:
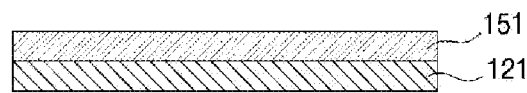
FIG. 5 is a cross-sectional view for explaining a second modification of a membrane member applied to the antimicrobial membrane according to the first and second embodiments of the present invention.
Figure 6:
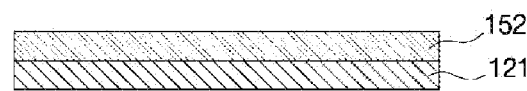
FIG. 6 is a cross-sectional view for explaining a third modification of a membrane member applied to the antimicrobial membrane according to the first and second embodiments of the present invention.

In some embodiments of the present invention, referring to FIGS. 5 and 6, a plurality of pores are formed in the first membrane member 121, respectively, and a nanofiber web 151 formed by accumulating the nanofibers containing dopamine having a functional group capable of adsorbing heavy metal ionic foreign substances, bacteria, viruses, and the like all of which are infiltrated from the outside, or a nanofiber web 152 formed by accumulating ion-exchange nanofibers may be further stacked on first membrane member 121. Here, preferably, one surface of the first membrane member 121 is close to the wound, and the nanofiber webs 151 and 152 are laminated on the other surface of the first membrane member 121. Of course, the opposite can also exist.

As shown in FIG. 5, the nanofiber web 151 made by accumulating nanofibers containing dopamine is laminated on the first membrane member 121, and as shown in FIG. 6, the nanofiber web 152 made by accumulating ion-exchanged nanofibers is laminated on the first membrane member 121.

The nanofiber web 151 formed by accumulation of nanofibers containing dopamine is a nanofiber web produced by electrospinning a spinning solution containing a mixture of a dopamine monomer or polymer, a solvent, and a polymer.

Dopamine (i.e. 3,4-dihydroxyphenylalamine) has a structure in which —$NH_2$ and —OH are bonded to a benzene ring.

The functional groups attached to the dopamine contained in the nanofiber can be formed by a post-treatment such as UV irradiation, plasma treatment, acid treatment, and base treatment after forming a nanofiber web containing a dopamine monomer or polymer. Finally, the nanofiber web containing dopamine is in a state where the functional group is attached to the nanofiber.

The nanofiber web 152 made by accumulating the ion-exchanged nanofibers is a nanofiber web made by accumulating ion-exchanged nanofibers produced by electrospinning an ion-exchange solution. The ion-exchange solution can be defined as a solution synthesized by a synthetic process such as bulk polymerization of a polymer, a solvent, and ion-exchange functional groups.

Since the ion exchange functional groups are contained in ion exchange nanofibers, ionic foreign substances such as heavy metals, bacteria, and viruses which penetrate outside the antimicrobial dressing, are adsorbed to the ion exchange functional groups by substitution.

For example, when the ion exchange functional groups are $SO_3H$, and/or $NH_4CH_3$, the ionic foreign substances (for example, ionic heavy metal cation or heavy metal anion) contained in water are replaced with $H^+$ and/or $CH_3^+$ and adsorbed to the ion exchange functional groups.

Here, the ion exchange functional groups include a cation exchange functional group selected from a sulfonic acid group, a phosphoric acid group, a phosphonic group, a phosphonic group, a carboxylic acid group, an arsonic group, a selenonic group, an iminodiacetic acid group and a phosphoric acid ester group; or an anion exchange functional group selected from a quaternary ammonium group, a tertiary amino group, a primary amino group, an imine group, a tertiary sulfonium group, a phosphonium group, a pyridyl group, a carbazolyl group and an imidazolyl group.

Figure 7:
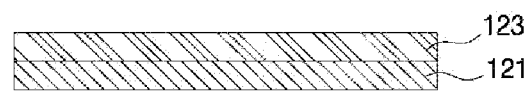
FIG. 7 is a cross-sectional view for explaining a fourth modification of a membrane member applied to the antimicrobial membrane according to the first and second embodiments of the present invention.

Referring to FIG. 7, the first and second membrane members 121 and 123 applied to the antimicrobial membrane according to the first and second embodiments of the present invention may have different diameters or different pore sizes of the nanofibers.

That is, the first membrane member 121 containing the antimicrobial substance have a nanofiber diameter that allows the water-soluble polymer to dissolve by the exudates secreted from the wound to have release properties, and the second membrane member 123 is preferably provided with extremely fine pores capable of providing excellent air permeability.

Therefore, the diameter of the nanofiber of the first membrane member 121 containing the antimicrobial substance is made thicker than the diameter of the nanofiber of the second membrane member 123 containing no antimicrobial substance.

Here, it is preferable that the diameter of the nanofiber of the first membrane member 121 should be 200 nm to 800 nm, and the diameter of the nanofiber of the second membrane member 123 should be less than 200 nm.

The pore size of the first membrane member 121 is 0.2 μm to 1 μm, and the pore size of the second membrane member 123 is preferably less than 0.2 μm.

Figure 8:
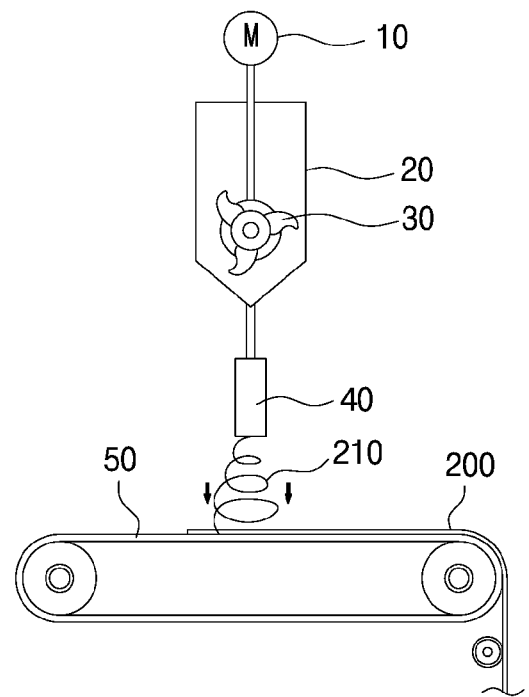
FIG. 8 is a schematic view for explaining an electrospinning apparatus for producing a membrane member of an antimicrobial dressing according to an embodiment of the present invention.

FIG. 8 is a schematic view for explaining an electrospinning apparatus for producing a membrane member of an antimicrobial dressing according to an embodiment of the present invention.

Referring to FIG. 8, an electrospinning apparatus for producing a membrane member of an antimicrobial dressing according to an embodiment of the present invention is characterized in that a stirring tank 20 for supplying a stirred spinning solution is connected to a spinning nozzle 40, a grounded collector 50 in the form of a conveyor that moves at a constant speed is placed in a lower portion of the electrospinning apparatus and spaced from the spinning nozzle 40, and the spinning nozzle 40 is connected to a high voltage generator.

Here, the water-soluble polymer, the water-insoluble polymer, the antimicrobial substance and the solvent are mixed with the stirrer 30 to prepare a spinning solution. Here, a pre-mixed spinning solution may be used before being put into the electrospinning apparatus without mixing the water-soluble polymer, the water-insoluble polymer, the antimicrobial substance and the solvent in the stirrer 30.

Thereafter, when a high voltage electrostatic force is applied between the collector 50 and the spinning nozzle 40, the spinning solution is made into ultrafine nanofibers 210 by the spinning nozzle 40 and spun onto the collector 50, and the nanofibers 210 are accumulated on the collector 50, to thus produce the nanofiber web 200 of the membrane member to be used for the antimicrobial dressing.

More specifically, the spinning solution discharged from the spinning nozzle 40 is discharged as the nanofibers 210 while passing through the spinning nozzle 40 charged by the high voltage generator, and the nanofibers 210 are sequentially laminated on the grounded collector 50 provided in the form of a conveyor moving at a certain speed to form the nanofiber web 200 for the antimicrobial dressing.

Figure 9:
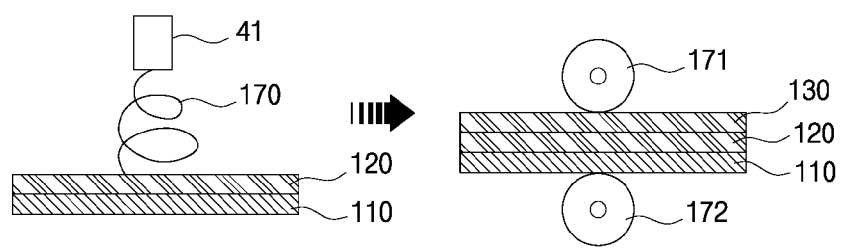
FIG. 9 is a schematic cross-sectional view illustrating a method of manufacturing an antimicrobial dressing according to an embodiment of the present invention.

Referring to FIG. 9, a method of manufacturing an antimicrobial dressing according to an embodiment of the present invention includes accumulating nanofibers containing a water-soluble polymer, a water-insoluble polymer, and an antimicrobial substance obtained by electrospinning on a first cover member 110 having a plurality of pores, so that an antimicrobial membrane 120 is laminated on the first cover member 110. Here, a spinning solution is discharged from a spinning nozzle 41 to form nanofibers 170.

Thereafter, a second cover member 130 is placed on the antimicrobial membrane 120, and then a stack of the second cover member 130, the antimicrobial membrane 120, and the first cover member 110 passes between rolls 171 and 172, and is calendered and laminated together.

Here, in some embodiments of the present invention, the antimicrobial membrane 120 is manufactured separately by electrospinning, and then the antimicrobial membrane 120 is interposed between the first and second cover members 110 and 130, followed by calendering and laminating, to thereby produce an antimicrobial dressing.

While the present invention has been particularly shown and described with reference to exemplary embodiments thereof, by way of illustration and example only, it is clearly understood that the present invention is not to be construed as limiting the present invention, and various changes and modifications may be made by those skilled in the art within the protective scope of the invention without departing off the spirit of the present invention.

INDUSTRIAL APPLICABILITY

The present invention is applied to an antimicrobial dressing for treating a wound, which can release an antimicrobial substance slowly by using a water-soluble polymer dissolved in an exudate to reduce the amount of the antimicrobial substance contacting the wound, thereby maximizing the antimicrobial characteristic on the surface of the wound.

What is claimed is:

1. An antimicrobial dressing comprising:
a first cover member having a plurality of pores formed therein;
an antimicrobial membrane laminated on the first cover member and having a plurality of pores formed therein, the antimicrobial membrane being formed of accumulated nanofibers, each of accumulated nanofibers being made of a mixture of a water-soluble polymer, a water-insoluble polymer, and an antimicrobial substance, wherein the water-soluble polymer of the accumulated nanofibers is configured to be dissolved by an exudate secreted from a user's wound, the antimicrobial substance of the accumulated nanofibers is configured to be released due to dissolution of the water-soluble polymer, and the water-insoluble polymer of the accumulated nanofibers is configured to maintain a structure of the antimicrobial membrane while dissolving the water-soluble polymer and releasing the antimicrobial substance; wherein the antimicrobial membrane is a multilayer structure of which water-soluble polymer content gradually increases towards the first cover member; and
a second cover member laminated on the antimicrobial membrane and having a plurality of pores formed therein,
wherein the first cover member is configured to be contacted with the user's wound, and the second cover member is configured to be exposed to an external air.

2. The antimicrobial dressing of claim 1, wherein the antimicrobial substance is one of a silver nanomaterial, a silver particle, and a natural antimicrobial substance.

3. The antimicrobial dressing of claim 1, wherein the water-soluble polymer is at least one or a mixture of two or more selected from the group consisting of PVA (polyvinyl alcohol), PVP (polyvinyl pyrrolidone), PEO (polyethylene oxide), CMC (carboxyl methyl cellulose), starch, PAA (polyacrylic acid) and a hyaluronic acid.

4. The antimicrobial dressing of claim 1, wherein the first cover and the second cover member are made of one of a nonwoven fabric, a fabric, and a mesh.

5. The antimicrobial dressing of claim 1, wherein the antimicrobial membrane comprises: a support member; a first membrane member on one surface of the support member, the first membrane member formed of first accumulated nanofibers made of the mixture; and a second membrane member on the other surface of the support member, the second membrane member formed of second accumulated nanofibers made of the water-insoluble polymer, wherein the first membrane member is laminated on the first cover member.

6. The antimicrobial dressing of claim 5, wherein the support member is made of one of a nonwoven fabric, a fabric, and a mesh.

7. The antimicrobial dressing of claim 5, wherein the first membrane member includes a plurality of pores, and further includes a nanofiber web stacked thereon,
wherein the nanofiber web is formed of third accumulated nanofibers containing dopamine having a functional group capable of adsorbing ionic foreign substances, bacteria, and viruses, or
wherein the nanofiber web is formed of accumulated ion-exchange nanofibers.

8. The antimicrobial dressing of claim 5, wherein the first accumulated nanofibers and the second accumulated nanofibers have diameters and pore sizes different from each other.

9. The antimicrobial dressing of claim 5, wherein the first accumulated nanofibers have a diameter in a range from 200 nm to 800 nm, and the second accumulated nanofibers have a diameter less than 200 nm.

10. The antimicrobial dressing of claim 5, wherein the first membrane member has pores having a size in a range from 0.2 μm to 1 μm, and the second membrane member has pores having a size of less than 0.2 μm.

11. The antimicrobial dressing of claim 1, wherein the antimicrobial membrane comprises: a first membrane member made of first accumulated nanofibers made of the mixture; and a second membrane member on the first membrane member, the second membrane member formed of second accumulated nanofibers made of the water-insoluble polymer, wherein the first membrane member is laminated on the first cover member.

12. The antimicrobial dressing of claim 11, wherein the first membrane member is a multilayer structure of which water-soluble polymer content gradually increases towards the first cover member.

13. The antimicrobial dressing of claim 11, wherein the first membrane member includes a plurality of pores, and further includes a nanofiber web stacked thereon,
wherein the nanofiber web is formed of third accumulated nanofibers containing dopamine having a functional group capable of adsorbing ionic foreign substances, bacteria, and viruses, or
wherein the nanofiber web is formed of accumulated ion-exchange nanofibers.

14. The antimicrobial dressing of claim 11, wherein the first accumulated nanofibers and the second accumulated nanofibers have diameters and pore sizes different from each other.

15. The antimicrobial dressing of claim 11, wherein the first accumulated nanofibers have a diameter in a range from 200 nm to 800 nm, and the second accumulated nanofibers have a diameter less than 200 nm.

16. The antimicrobial dressing of claim 11, wherein the first membrane member has pores having a size in a range from 0.2 μm to 1 μm, and the second membrane member has pores having a size of less than 0.2 μm.

* * * * *